(12) United States Patent
Alshehri et al.

(10) Patent No.: US 12,053,342 B1
(45) Date of Patent: Aug. 6, 2024

(54) ENDODONTIC MICRO SURGICAL SUCTION TIP FOR MANAGEMENT OF A NECROTIC TOOTH

(71) Applicant: KING SAUD UNIVERSITY, Riyadh (SA)

(72) Inventors: Mohammed Abdullah Alshehri, Riyadh (SA); Omar Mohammed Alshehri, Riyadh (SA); Ibrahim Rshood Alqwizany, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/620,323

(22) Filed: Mar. 28, 2024

(51) Int. Cl.
  *A61C 5/40* (2017.01)
  *A61C 5/50* (2017.01)
  *A61C 17/02* (2006.01)
  *A61M 1/00* (2006.01)

(52) U.S. Cl.
  CPC ............ *A61C 5/40* (2017.02); *A61C 5/50* (2017.02); *A61C 17/0208* (2013.01); *A61M 1/774* (2021.05)

(58) Field of Classification Search
  CPC .... A61C 5/40; A61C 5/50; A61C 5/55; A61C 5/62; A61C 17/0208; A61M 1/77; A61M 1/772; A61M 1/774; A61M 1/85; A61M 3/0283; A61M 5/19; A61M 5/31581
  See application file for complete search history.

(56) References Cited

U.S. PATENT DOCUMENTS

| | | | |
|---|---|---|---|
| 6,245,046 B1 * | 6/2001 | Sibbitt | A61M 5/31511 604/191 |
| 6,641,394 B2 * | 11/2003 | Garman | A61C 5/64 433/91 |
| 7,549,861 B2 * | 6/2009 | Ruddle | A61C 5/40 417/571 |
| 7,674,247 B2 * | 3/2010 | Fojtik | A61M 5/19 222/391 |
| 10,099,244 B2 * | 10/2018 | Pfahnl | A61M 5/3148 |
| 10,265,470 B2 * | 4/2019 | Brandeis | A61M 5/31511 |
| 11,305,060 B2 * | 4/2022 | Brandeis | A61M 1/774 |
| 2003/0069549 A1 * | 4/2003 | MacMahon | A61M 1/67 604/266 |
| 2007/0244425 A1 | 10/2007 | Pond | |
| 2010/0190133 A1 * | 7/2010 | Martinez | A61C 17/0208 604/319 |
| 2017/0209649 A1 * | 7/2017 | Wei | A61M 5/31581 |
| 2018/0036105 A1 | 2/2018 | Maxwell et al. | |
| 2022/0040398 A1 | 2/2022 | Grasso et al. | |

FOREIGN PATENT DOCUMENTS

WO  202351751 A1  4/2023

* cited by examiner

*Primary Examiner* — Edward Moran
(74) *Attorney, Agent, or Firm* — Nath, Goldberg & Meyer; Joshua B. Goldberg

(57) ABSTRACT

A system and method for treating a necrotic tooth in a root canal and includes using a dual function double barrel reciprocating syringe in conjunction with a dual channel needle to provide both an irrigant for irrigation and aspiration of the irrigant and organic debris within the necrotic tooth. Once optimally positioned and secured in place by a rubber seal, root canal of the tooth can be treated through irrigation and aspiration of the dual channel needle.

9 Claims, 3 Drawing Sheets

ENDODONTIC MICRO SURGICAL SUCTION TIP FOR MANAGEMENT OF A NECROTIC TOOTH

BACKGROUND

1. Field

The present disclosure relates to a method and apparatus for the treatment of a necrotic tooth using an endodontic microsurgical suction needle tip for performing dental procedures, and specifically for delivering and aspirating irrigants in a root canal therapy.

2. Description of the Related Art

Endodontics has become an important part of dentistry. Prior to common use of endodontic procedures, an abscessed tooth was typically treated only by extraction of the tooth. However, since the advancement of endodontics, abscessed teeth can be successfully treated to permit retention by a patient, for greatly increased health and physiological benefit. Endodontics has been one of the great advances in modern medicine.

The endodontic preparation of a root canal typically includes opening the root canal through the coronal area of the tooth and thereafter manipulating files and reamers within the root canal to physically remove as much as possible of the pulpal material. The pulpal material is typically infected or necrotic, that is, dead material; and any such material that remains in the root canal after the procedure is completed is a source of potential infection. For this reason, proper treatment of a root canal attempts to remove as much of the necrotic pulpal material as is possible.

By use of files and reamers, a substantial portion of such pulpal material can be removed; however, it is virtually impossible in most cases to remove all such material by physical manipulation of tools within the canal. For this reason, in recent times procedures have been developed wherein the root canal is irrigated or flushed with a fluid to remove and/or neutralize organic pulpal material that remains after files and reamers have been employed. The pulpal material and fluid can then be removed through aspiration.

To preserve a tooth that has a diseased pulp cavity, it is necessary to prevent bacterial proliferation within the pulp canal of the tooth by removing the diseased or necrotic pulp material from the pulp canal. After the pulp material has been removed or extirpated from a tooth, the pulp cavity is typically filled or obturated with a material such as gutta percha to occlude the pulp cavity and a viscous sealer to aid in sealing the pulp cavity. This procedure is referred to as root canal therapy. Root canal cleaning is generally achieved by hand or mechanical instrumentation with files that are configured to bore and cut.

It is also common during the root canal procedure to irrigate a pulp cavity and the various root canals involved using an endodontic irrigator tip. Irrigation assists in removing debris and necrotic material cut by the endodontic files and reamers. Disinfecting solutions can also be employed in irrigation, thereby disinfecting the pulp cavity and root canals during the operative procedure.

Another problem associated with root canal therapy is apical perforation. Before a file or irrigation tip is inserted into a root canal, the length of the root canal is determined to identify a suitable working length for the file or irrigation tip. Generally, the working length corresponds to the distance from a fixed reference position on the crown of a tooth to a location above the apical constriction of the root canal. Radiography is the most common method for measuring the length of the root canal. The preoperative x-ray image of the diseased tooth is taken from the front or back of the tooth. The length of the root canal and the desired working length of the cannula to be placed therein are then determined.

Perforation of the apex of a root canal can result from the use of files or endodontic irrigation tips that are too long. Such apical perforations typically result from an error in estimating the length of a root canal or the working length of the cannula. Similarly, the apex can be perforated by extrusion of infected material through the apex due to the force exerted by the file or tip on the material as the file or tip is pushed downward to reach the apex. In addition to exposing the tissue surrounding the tooth to the infected material, apical perforations also substantially complicate subsequent healing of the root canal.

The possibility of perforating the apex is particularly frustrating because it is often desirable to deliver fluid that reaches the apex in order to disinfect the apex and dissolve necrotic tissue therein. However, certain fluids are too viscous or the surface tension prevents certain fluids from reaching the apex if delivered too far above the apex. Sodium hypochlorite, for example, is a widely used, strong disinfectant that, because of surface tension issues, can stick in the pulp chamber rather than reaching the apex if not delivered with precision from the appropriate location above the apex.

Moreover, to truly irrigate necrotic debris it is often advisable to have the irrigant be delivered distal to the debris. Attempts to deliver the solution from the appropriate location, however, may result in the perforation of the apex. The possibility of perforating the apex of the root canal with an endodontic file is sometimes prevented by employing a removable stop that is placed about the distal insertion end of the file and pushed a desired distance toward the proximal gripping end of the file. Such adjustable stops, however, are prone to slip and slide along the longitudinal axis of the file, thereby allowing perforation of the apex. In addition, placing a stop on the file requires handling of the file prior to use, possibly contaminating the file. One solution to this was the use of a movable collar or neck on the irrigation probe as described in U.S. Pat. No. 6,079,979 to Riitano. This probe is similar to the probe described in U.S. Pat. No. 6,422,865 to Fisher, again without a suction or aspirating portion. However, this movable collar does not address the problem of the caustic irrigant solution as described below.

One of the greatest complications of endodontic root canal irrigation is leakage of the irrigant fluid, which is often sodium hypochlorite or another caustic antiseptic solution, onto the mucosa of the mouth (gums, gingivae, etc.). For example, injection of the irrigant into the periapical tissues can cause necrosis of these tissues, i.e., bone and periodontal ligament, causing a severe and painful chemical burn. Often an operator must put the aspirating tip of a surgical vacuum handle directly on the surface of the crown next to the irrigator needle in order to aspirate the waste irrigant solution before it spills onto the oral mucosa and causes a severe chemical burn.

For practitioners that do not use sterilizing irrigant, but rather use water or normal saline, the greatest danger is splash-back onto the operator, increasing their danger of acquiring hepatitis, HIV, and other infectious diseases. Thus, simultaneous aspiration is important in this instance also. This is a very cramped environment with both the irrigating syringe and probe and the surgical aspiration vacuum handle in the patient's mouth. U.S. Pat. Appl. No. 2006/0259014 to Yarger describes a typical aspirator sleeve and handle for this purpose. U.S. Pat. No. 4,272,288 to Yoshii et al. describes an irrigation pen that permits continuous irrigation of a root canal, but no simultaneous aspiration.

U.S. Pat. No. 3,807,048 to Malmin describes an endodontic gun that can inject, irrigate, and evacuate for this purpose, but it is not a simple syringe technology, involves the use of valves, and can only sequentially irrigate and aspirate, rather than simultaneously irrigate and aspirate. U.S. Pat. Nos. 5,203,697, 5,490,779, and 5,540,587 to Malmin also describe an endodontic device that can aspirate and inject, but again sequentially, rather than simultaneously. U.S. Pat. No. 4,993,947 to Grosrey demonstrates an irrigation needle surrounded by a vacuum sheath, but the device does not use a syringe for the irrigant solution nor does the vacuum sheath move along the shaft of the needle.

What is needed is a method and device for an irrigation-aspiration syringe that can deliver irrigant solution to the apex of the tooth and simultaneously aspirate necrotic debris and spent irrigant solution before it burns the mouth or splashes back on the operator while at the same time permitting moment to moment adjustment of probe depth in the tooth and sheath position on the probe while using standard irrigation needles and conventional syringes if desired. This device preferably is amenable to low-cost mass production, requires minimal hand assembly, and should have a low risk of accidental needlestick while inserting the irrigation probe into the sheath.

SUMMARY

This present subject matter relates to dental instruments and particularly to endodontic instruments, systems, and procedures for treating a tooth root canal in which the root canal is cleansed of bacteriological materials by physical and acoustic debridement and flushing with an irrigation solution. An embodiment relates to the apparatus and equipment for providing irrigation to remove diseased and necrotic tissue, and providing aspiration to remove the irrigation solution and resulting debris.

An endodontic or periodontic irrigation and aspiration device as described herein comprises a conventional or non-conventional syringe in a stacked or double-barrel configuration for a needle.

In a first aspect, the present subject matter relates to a penetration or tract wound irrigation and aspiration device comprising a conventional or non-conventional syringe with a dual barrel, with a first barrel associated with an aspiration channel and a second barrel which abuts said first barrel where the second barrel is associated with an irrigation channel. The first barrel and the second barrel each have a side vent providing an opening to the channel within each needle barrel that connects back to a tube connector such that each tube within the tube collector connects to a respective syringe.

A second aspect of the present subject matter relates to the method which, when implemented with the device, performs the functions of irrigating and aspirating a root canal of a necrotic tooth of a patient.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF EMBODIMENTS

The following detailed description is merely exemplary in nature and is not intended to limit the described embodiments or the application and uses of the described embodiments. Any implementation described herein with the words "exemplary" or "illustrative" is not necessarily construed as preferred or advantageous over other implementations. All of the implementations described below are exemplary implementations provided to enable persons skilled in the art to make or use the embodiments of the disclosure and are not intended to limit the scope of the disclosure, which is defined by the claims. For the purposes of the description herein, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed therein are not to be considered as limiting, unless the claims expressly state otherwise.

Figure 1:
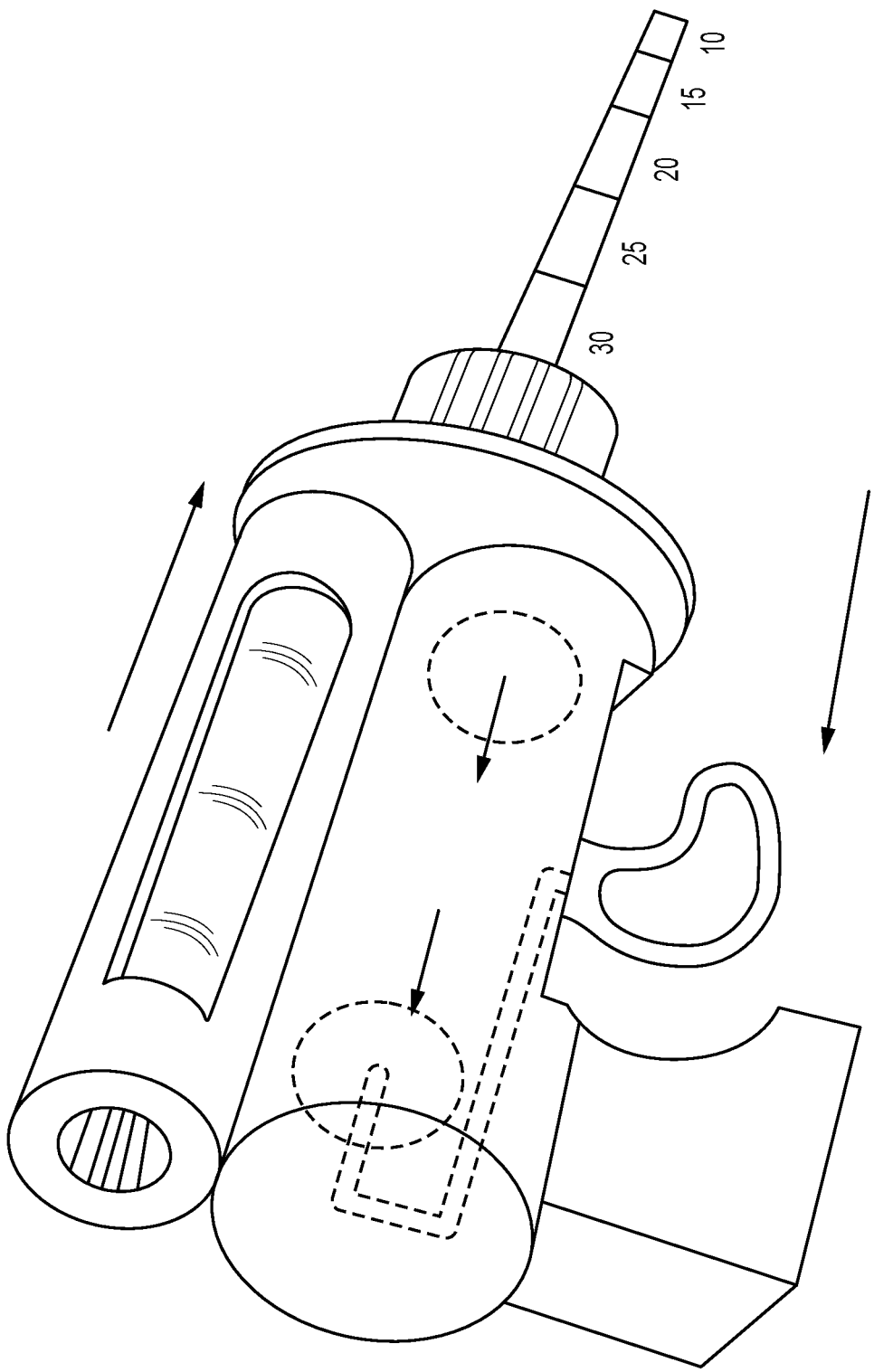
FIG. 1 is a rear view of the hand-held dual syringe where both irrigation and aspiration are provided by using a single triggering mechanism.
Figure 2:
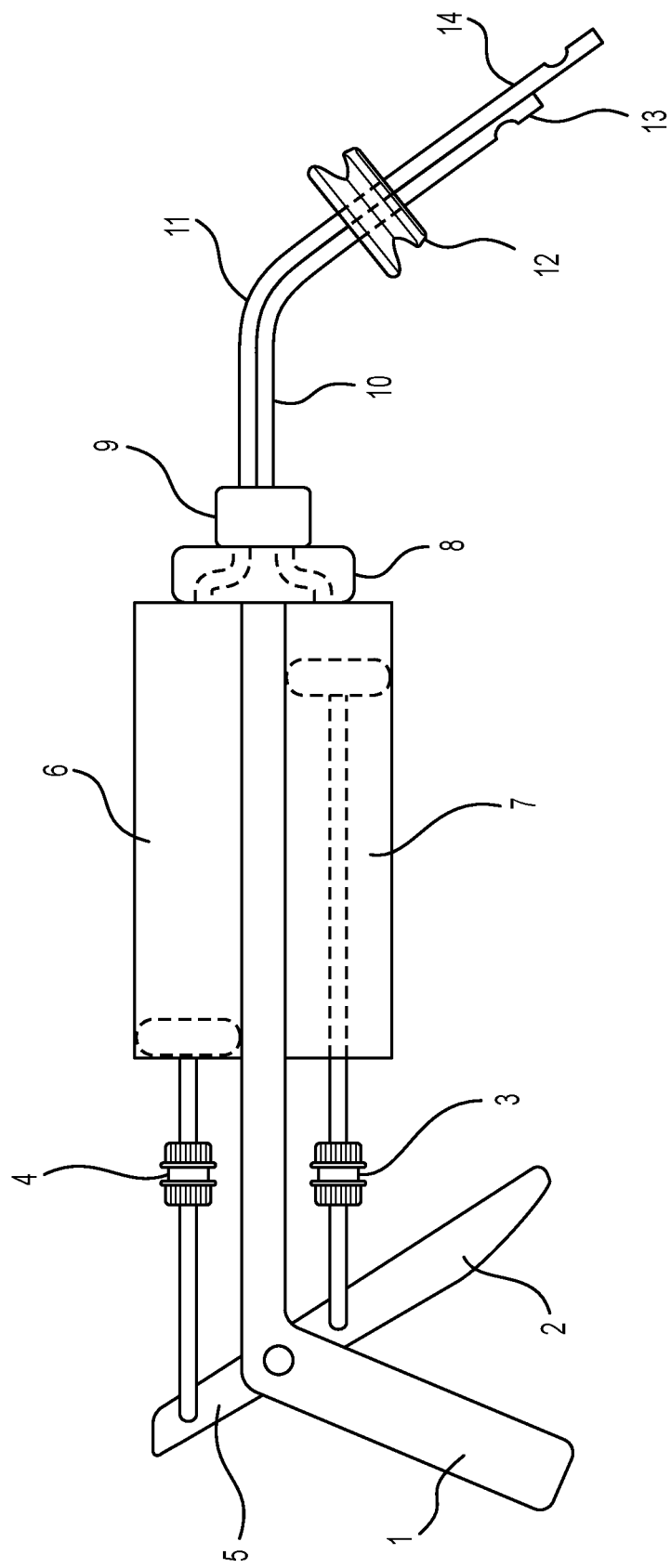
FIG. 2 is a side view of the hand-held dual syringe which also depicts the dual-barrel needle attachment.

FIGS. 1 and 2 are schematic illustrations of a first embodiment of the device including a double barrel reciprocating syringe that simultaneously provides for irrigant injection and aspiration. In the embodiment of FIG. 2, a double functional barrel reciprocating syringe device includes a handle consisting of a gun handle grip 1 and an upper handle 5 which terminates in a trigger portion 2.

As shown in FIG. 2, the gun handle grip 1 and the upper handle are connected to each other at a pivot point about which both the gun handle grip and the upper handle can be squeezed together such that the gun handle grip 1 and the trigger portion 2 are moved closer together when squeezed together by a user's hand (not shown). The gun handle grip 1 bends after the pivot point and forms a mounting bar that provides support and alignment to a first barrel 6 and a second barrel 7 of the double barrel reciprocating syringe. The upper handle 5 is also connected to a first plunger and a upper tightening screw 4 and a second plunger and a lower tightening screw 3. With this squeezing motion as shown in FIG. 1, the upper tightening screw 4 of a first plunger of the upper or first barrel 6 moves the first plunger through the volume of the first barrel 6 causing the irrigant contained within said first barrel to exit the first barrel 6 and thereby enter the tube collection center 8 and travel down the first channel 11 of the dual barrel needle towards its distal end 14 where the irrigant is expelled from the side vent to irrigate the root canal.

At the same time, a reverse action of the lower tightening screw 3 of a second plunger of the lower or second barrel 7 of the double barrel reciprocating syringe moves the plunger towards the gun handle grip 1 thereby enlarging the volume of the second barrel 7 such that aspiration of the irrigant and/or other organic debris in the root canal is provided. This can allow the irrigant and/or other debris to enter the volume of the lower or second barrel 7 of the double barrel syringe by entering the side vent of the second channel 10 of the dual barreled needle and to travel up away from the distal end 13 of the second channel 10 of the dual barreled needle towards the collection center 8 and finally settle into the volume the second barrel 7. The distal end of the dual barreled needle is held in place within the necrotic tooth structure by a rubber seal 12 which ensures that the dual channel needle is stable during the procedure. This dual action through the use of a single trigger squeeze is shown in FIG. 1. Accordingly, with two functional barrels, the dual functional barrel design of the double barrel reciprocating syringe permits twice the amount of volume to be transferred with a complete stroke cycle compared to the single functional syringe barrel designs.

Additionally, to function as a pump, the barrels may be fitted with unidirectional valves. The direction of the one-way valves determines whether the syringe functions as an aspiration, or irrigation, pump. When the direction of the valve systems are opposite in the two barrels, an irrigation pump is created. The power results from use of forceful flexion of not only intrinsic muscles of the hand, but also powerful flexors of the forearm. Since the motion is smooth and in one direction, there is no rotation, twist, or other loss of control, resulting in a smooth aspiration or irrigation with excellent control. Injection with the syringe of the present disclosure is identical to that of a standard syringe, using powerful flexor muscles of the hand and forearm. Injection with this aspiration syringe may be easily accomplished with one hand, freeing up the other hand for other necessary tasks or procedures.

The reciprocating syringe device as disclosed herein can have the following advantages over conventional syringes: 1) single-handed aspiration may be accomplished easily; 2) the other hand is freed and may be used for other tasks; 3) the power of the aspiration is maximized by the use of hand and forearm flexors rather than weak extensors of the thumb; 4) there is no rotational twist during forceful movement of the plunger resulting in markedly improved performance over other single-handed aspiration techniques; 5) the same hand grip position may be used throughout the aspiration/injection cycles unlike other single-hand techniques; 6) for procedures that require constant aspiration with one hand, this syringe is ideal because it may be held in an aspiration position with or without a locking device; and 7) both single functional barrel and double functional barrel versions may be converted into single-hand-held pumps by the addition of unidirectional valves.

Figure 3:
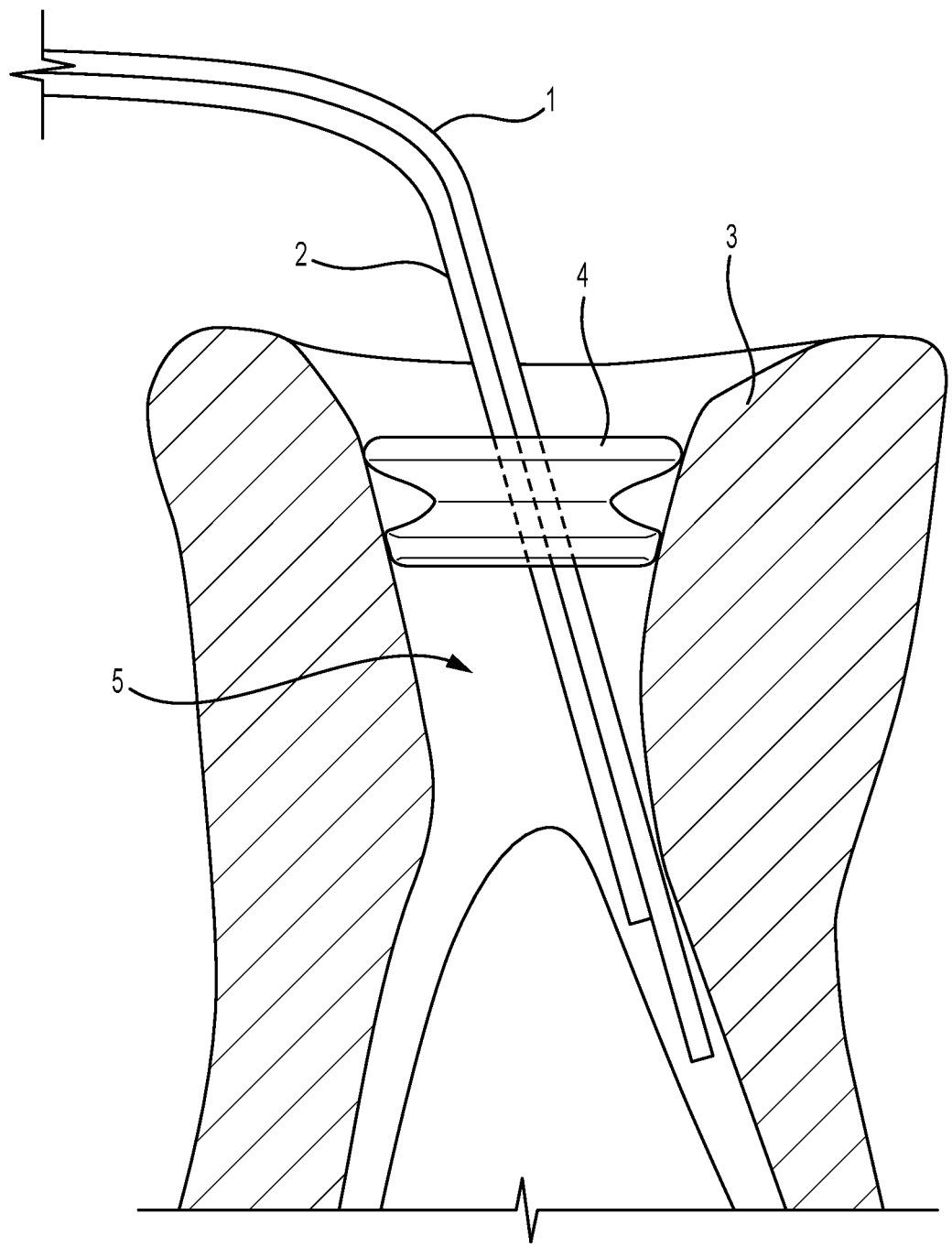
FIG. 3 depicts the optimal positioning of the dual-barrel needle with a root canal of a necrotic tooth.

FIG. 3 shows the distal end of the double barrel reciprocating syringe deployed at the site of a necrotic tooth 3 of a patient where the rubber seal 4 is inserted into the pulp chamber 5 of the necrotic tooth 3 until it snuggly fits against the interior walls of the pulp chamber 5. At this optimal position, the rubber seal 4 provides two benefits. First it ensures that the first channel 1 and the second channel 2 of the dual channel needle remain stable throughout the procedure. And second, the rubber seal ensures that the distal end of the first channel 1 and the second channel 2 of the dual channel needle doesn't penetrate the apex of the root canal of the pulp chamber. The rubber seal 4 is made of two truncated conical segments (i.e. frustums) joined together. In the center of the rubber seal 4 is a smaller aperture through which the first channel 1 and the second channel 2 of the dual channel needle are inserted such that the dual channel needle's distal ends can be inserted into the root canal as shown in FIG. 3. Also shown in FIG. 3 is a detailed depiction of the rubber seal 4, where the topmost first frustum is inverted with respect to the second frustum. That is, the rubber seal 4 has a first frustum that has its smaller circular bottom base connecting to the smaller circular top base of the second frustum. This arrangement also provides wider points of contact, and therefore, improved stability, with respect to the interior walls of the necrotic tooth 3.

Although the above-described embodiments are manually operated, the present syringes may also be mechanically, motor, electrically, or computer-driven or controlled devices. For example, in a present syringe device having two barrels and one or more valves associated with each barrel, the reciprocal motion of the plungers for each of the barrels may be controlled with a crankshaft-like device which pushes one plunger down as it pulls the other plunger up. Such a crankshaft-like device may be powered in a variety of ways and such a crankshaft device may be used to operate all the plungers in embodiments of the present syringe device having multiple barrels. In embodiments which are not manually operated, finger flanges shown in the above-described manually operated embodiments may be eliminated and syringe barrel, barrels, guide tracks, etc., may be held in place relative to the plunger, plungers, reciprocating members, etc., by other means, such as mounting the syringe barrel in place. Although the above-described embodiments of the syringe device have been primarily described as being used as a dental device, this device may also be used in other applications such as industrial applications, automotive applications, and the like.

It is to be understood that the method and device for the treatment of a necrotic tooth is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A double barrel reciprocating syringe for treating a necrotic tooth of a patient comprising:
   a first barrel of the double barrel reciprocating syringe configured to hold a volume of irrigant;
   a second barrel of the double barrel reciprocating syringe configured to hold a volume of aspirant and/or organic debris;
   a handle apparatus comprising:
      a gun handle;
      an upper handle terminating in a trigger grip; and
      a pivot point connecting the gun handle and the upper handle;
   a first plunger and tightening screw arrangement with a first proximal end connected to the upper handle and a first distal end connected to the first barrel;
   a second plunger and tightening screw arrangement with a second proximal end connected to the upper handle and a second distal end connected to the second barrel;
   a tube collection center connected to a first opening of the first barrel and a second opening of the second barrel, respectively, at a proximal end of the tube collection center;
   a needle cap connector connected to the tube collection center at a proximal end of the needle cap collector; and
   a dual channel needle connected to the needle cap connector at a distal end of the needle cap connector, wherein the dual channel needle has a first channel for irrigation and a second channel for aspiration, and wherein a distal end the dual channel needle is configured to be inserted into a root canal of a patient's necrotic tooth and wherein a rubber seal is provided on the dual channel needle, wherein the rubber seal is configured to fit within a pulp chamber of the patient's necrotic tooth such that it abuts an interior surface of the pulp chamber and is positioned such that the distal end of the dual channel needle is prevented from penetrating an apex of the root canal.

2. The double barrel reciprocating syringe as recited in claim 1, wherein said gun handle bends after the pivot point and forms a mounting bar that provides support and alignment to the first barrel and the second barrel of the double barrel reciprocating syringe.

3. The double barrel reciprocating syringe as recited in claim 2, wherein the first channel for irrigation and the second channel for aspiration of the dual channel needle each have a side vent.

4. The double barrel reciprocating syringe as recited in claim 3, wherein the first plunger and the second plunger are caused to move when the trigger grip and the gun handle are squeezed together.

5. The double barrel reciprocating syringe as recited in claim 4, wherein said rubber seal is formed from two frustums.

6. The double barrel reciprocating syringe as recited in claim 5, wherein said first frustrum is inverted with respect to said second frustum.

7. The double barrel reciprocating syringe as recited in claim 6, where said first and second plungers move simultaneously.

8. The double barrel reciprocating syringe as recited in claim 7, wherein the first plunger moves across a first volume of the first barrel causing the irrigant to enter the first channel of the dual channel needle.

9. The double barrel reciprocating syringe as recited in claim 8, wherein the second plunger moves towards the handle of the double barrel reciprocating syringe of the first barrel causing the irrigant and/or organic debris to enter the second channel of the dual channel needle.

* * * * *